(12) United States Patent
Abe et al.

(10) Patent No.: US 6,479,478 B1
(45) Date of Patent: Nov. 12, 2002

(54) CARBAPENEM COMPOUNDS

(75) Inventors: Takao Abe, Sakado (JP); soh-ichi Kaneda, Shiki (JP); Kazuhiko Hayashi, Yokohama (JP)

(73) Assignee: Wyeth Lederle Japan, Ltd., Tokyo (JP)

( * ) Notice: Subject to any disclaimer, the term of this patent is extended or adjusted under 35 U.S.C. 154(b) by 0 days.

(21) Appl. No.: 09/786,718

(22) PCT Filed: Sep. 7, 1999

(86) PCT No.: PCT/JP99/04846

§ 371 (c)(1),
(2), (4) Date: Mar. 8, 2001

(87) PCT Pub. No.: WO00/15640

PCT Pub. Date: Mar. 23, 2000

(30) Foreign Application Priority Data

Sep. 10, 1998 (JP) ............................................ 10-257051

(51) Int. Cl.⁷ .................. C07D 477/20; A61K 31/4178; A61K 31/505; A61P 31/04
(52) U.S. Cl. ............... 514/210.12; 540/350; 548/314.7; 548/324.1
(58) Field of Search ............................ 540/210.12, 350

(56) References Cited

U.S. PATENT DOCUMENTS 3,950,357 A  4/1976  Kahan et al. .......... 260/326.27
4,921,852 A  5/1990  Murata et al. ............... 514/210
6,180,621 B1 * 1/2001  Kawamoto ............. 514/210.12

FOREIGN PATENT DOCUMENTS

| EP | 0 632 039 | 1/1995 |
| JP | 63-170379 | 7/1988 |
| JP | 2-15081 | 1/1990 |
| JP | 8-53453 | 2/1996 |

* cited by examiner

Primary Examiner—Mark L. Berch
(74) Attorney, Agent, or Firm—Crowell & Moring LLP

(57) ABSTRACT

It is provided carbapenem compounds represented by the following formula (I):

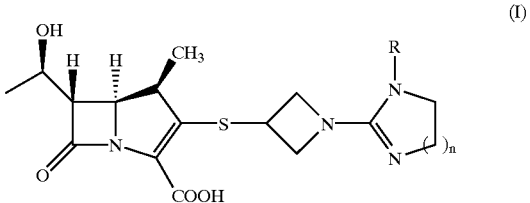

wherein
R is hydrogen atom, or substituted or unsubstituted lower alkyl group; and,
n is an integer of 1 or 2, or a pharmaceutically acceptable salt thereof, and an antibacterial compositions containing these compounds as an active ingredient. These carbapenem compounds exhibit potent antibacterial activities and are excellent in the resistance against renal dehydropeptidase.

6 Claims, No Drawings

CARBAPENEM COMPOUNDS

TECHNICAL FIELD

The present invention relates to carbapenem antibiotics and, more particularly, to carbapenem compounds having a β-orientated methyl group introduced at 1-position and 1-[(heterocyclyl)-azetidin-3-yl]thio group at the 2-position of carbapenem skeleton, and to antibacterial compositions containing the same as an active ingredient.

BACKGROUND ART

Since the discovery of thienamycin [U.S. Pat. No. 3,950,357; J. Am. Chem. Soc., 100, 313(1987)], there have been proposed many carbapenem antibiotic substances, and among them imipenem (INN) have been developed as a practically useful carbapenem antibiotic substance, and is widely used in clinical field.

Although the imipenem, developed at first as carbapenem antibiotic substance, exhibits wide antibacterial activities against gram positive or negative bacteria, it possesses the disadvantage that it is decomposed within a short period of time by renal dehydropeptidase (DHP) in the living body. For this reason, imipenem cannot be administered singly, and must be used in combination with a DHP inhibitor in order to control its decomposition leading to inactivation. Therefore, its formulation for clinical administration is a combination with cilastatin (INN) that is a DHP inhibitor.

An antibacterial agent preferred for practical clinical use; however, is one that alone can demonstrate antibacterial activity. Furthermore, the DHP inhibitor to be combined with the antibiotic could exert undesirable action on tissues of the living body. For these reasons, the combined use should be avoided wherever possible. Thus, there has been a growing demand for a carbapenem compound having sufficiently high degrees of both antibacterial activity and resistance to DHP.

There were proposed some carbapenem compounds of the type that could achieve the above-mentioned objectives. Such carbapenem compounds are 1-methylcarbapenem compounds in which a methyl group is introduced at the 1-position of the carbapenem skeleton, and it is reported that these carbapenem compounds are not only resistant to DHP but also more chemically stable than those having no methyl group at the 1-position of the carbapenem skeleton.

Under these circumstances, many researchers have specifically attempted to modify a side-chain substituent at 2-position of 1-methylcarbapenem compounds, and as a result, meropenem and biapenem are proposed for the carbapenem antibiotics that can be administered singly.

Although, the carbapenem compounds possess a potent antibacterial activity with a broad spectrum, it is anticipated that the resistant strain, which is a problem in the field of β-lactam antibiotics, will appear. That is, it is well anticipated for new carbapenem antibiotics to be effective at first, but long time clinical use of it will gradually cause the resistant to appear. Therefore, there always is constant demand for development of new compounds having excellent antibacterial activity in the antibacterial field.

Under these circumstances, it is the purpose of the present invention to provide new carbapenem compounds having high antibacterial activities and a strong action of inhibiting β-lactamase as well as improved resistance to DHP.

DISCLOSURE OF INVENTION

Accordingly, one subject of the present invention is to provide carbapenem compounds represented by the following formula (I):

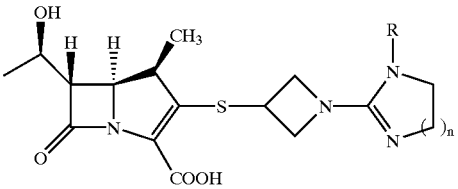

wherein

R is hydrogen atom, or substituted or unsubstituted lower alkyl group; and, n is an integer of 1 or 2, or a pharmaceutically acceptable salt thereof.

Another subject of the present invention is to provide ester compounds of formula (I), in which carboxylic acid group at 3-position is converted to ester form by various kinds of ester residues. These ester residues may be conventional ester residues, which are widely used for ester moieties for carboxylic group in this field.

The carbapenem compounds according to the present invention are characterized in that the substituent at the 2-position of 1-methyl carbapenem skeleton is specific 1-heterocyclyl-azetidin-3-ylthio group, which is never demonstrated for substituent for 2-position, and have superior antibacterial activities.

Therefore, still another subject of the present invention is to provide an antibacterial agent containing the carbapenem compounds represented by the formula (I) above, ester thereof or pharmaceutically acceptable salt thereof claimed in claim 1 as an active ingredient.

BEST MODE FOR CARRYING OUT THE INVENTION

The present invention is described in more detail in the following. The terms used throughout the present specification have following meanings.

The term "lower" qualifying a group or a compound means that the group or the compound qualified has 1 to 7, preferably 1 to 4, carbon atoms.

The term "lower alkyl group" stands for a linear or branched alkyl group such as methyl, ethyl, n-propyl, isopropyl, n-butyl, isobutyl, sec-butyl, tert-butyl, n-pentyl, isopentyl, n-hexyl, isohexyl, n-heptyl, isoheptyl and so on.

Substituents, which can substitute to said lower alkyl group, are hydroxy group; lower alkoxy group; halogen atom such as chlorine, bromine, and so on; mono-substituted amino group; di-substituted amino group such as dimethylamino, diethylamino, methylethylamino, and the like; phenyl; substituted phenyl such as hydroxyphenyl, methylphenyl, dimethylphenyl, aminophenyl, aminomethylphenyl, nitrophenyl, and so on; nitro group; acetyl group, and the like.

When the carbapenem compounds of the present invention have an asymmetric carbon atom at the side chain of the 2-position, the isomers can be stereo-selectively obtained by using optically active starting materials, and each isomer can be isolated from the stereoisomeric mixture by usual method. Therefore, each isomer per se, as well as the stereoisomeric mixture, should be included in the compounds of the present invention.

The following are the typical carbapenem compounds of the present invention.

(1R,5S,6S)-2-[1-(1,3-imidazolin-2-yl)azetidin-3-yl]thio-6-[(R)-1-hydroxyethyl]-1-methylcarbapen-2-em-3-carbolic acid;

(1R,5S,6S)-2-[1-(1-methy-2-imidazolin-2-yl)azetidin-3-yl]-thio -6-[(R)-1-hydroxyethyl]-1-methylcarbapen-2-em-3-carbolic acid;

(1R,5S,6S)-2-[1-(1,4,5,6-tetrahydropyrimidin-2-yl) azetidin-3-yl]thio -6-[(R)-1-hydroxyethyl]-1-methylcarbapen-2-em-3-carbolic acid;

(1R,5S,6S)-2-[1-(1-methyl-1,4,5,6-tetrahydropyrimidin-2-yl) azetidin-3-yl]thio-6-[(R)-1-hydroxyethyl]-1-methylcarbapen-2-em-3-carbolic acid;

(1R,5S,6S)-2-[1-(1-(4-aminomethylbenzyl)-2-imidazolin-2-yl) azetidin-3-yl]thio-6[-(R)-1-hydroxyethyl]-1-methylcarbapen-2-em-3-carbolic acid.

Examples of the pharmaceutically acceptable salt of carbapenem compound of the present invention include nontoxic inorganic or organic salts thereof. The inorganic salts may include alkali metal salt such as sodium, potassium and the like; alkali earth metal salt such as calcium, magnesium and the like; and ammonium salt thereof. The organic salts may include triethylamine, pyridine, picoline, ethanolamine, triethanolamine, dicyclohexyl amine, N,N'-dibenzyl-ethylenediamine and the like.

Furthermore, the carbapenem compounds of the present invention may be converted into a pharmaceutically acceptable acid addition salt thereof with organic or inorganic acids. Examples of inorganic acids include hydrochloric acid, nitric acid, hydrobromic acid, sulfuric acid and phosphoric acid. Examples of organic acids include organic acid such as formic acid, acetic acid, trifluoroacetic acid, maleic acid, tartaric acid, methanesulfonic acid, benzenesulfonic acid and so on; and basic or acidic amino acid such as arginine, aspartic acid, glutamic acid and the like.

The ester compound of the present invention may include ester compound prepared by the ester residue mentioned later.

The carbapenem compound of the present invention may be prepared in accordance with the processes as illustrated by the reaction scheme A shown below.

Reaction Scheme A

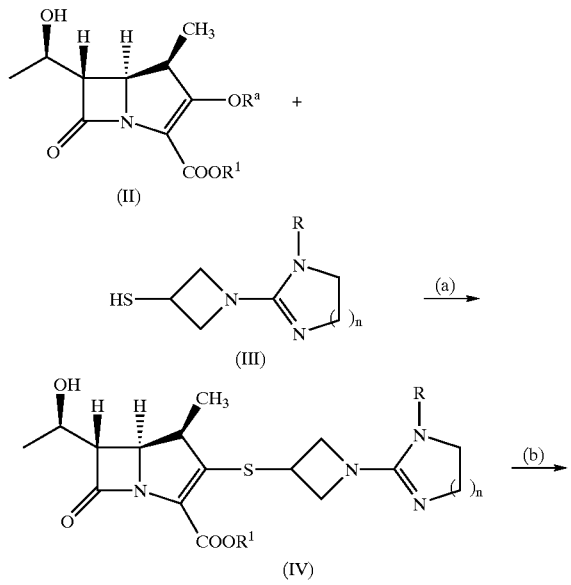

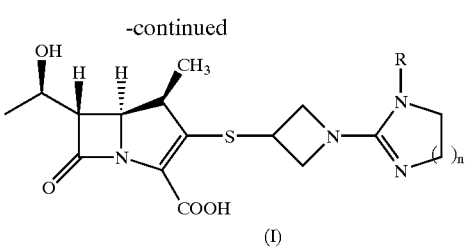

(I)

wherein $R^a$ is acyl group; $R^1$ is carboxyl protecting group; and R and n have the same meanings as above.

The term "acyl group" represented by $R^a$ may be, in a narrow sense, a moiety obtained by removing the hydroxyl group from the carboxyl group of an organic carboxylic acid as well as, in a broader sense, any acyl group derived from an organic sulfonic acid or an organic phosphoric acid. Such an acyl group may include, for example, a lower alkanoyl group such as acetyl, propionyl, butyryl or the like; a (halo) lower alkyl sulfonyl group such as methanesulfonyl, trifluoromethanesulfonyl or the like; a substituted or unsubstituted arylsulfonyl group such as benzenesulfonyl, p-nitrobenzenesulfonyl, p-bromobenzenesulfonyl, toluenesulfonyl, 2,4,6-triisopropylbenzenesulfonyl or the like; and diphenylphosphoryl.

The term "caroboxyl protecting group" represented by $R^1$ may stands for ester group. Examples include lower alkyl ester such as methyl ester, ethyl ester, n-propyl ester, iso-propyl ester, n-, iso- or tert-butyl ester, n-hexyl ester or the like; aralkyl ester such as benzyl ester, p-nitrobenzyl ester, o-nitrobenzyl ester, 2,4-dinitrobenzyl ester, p-chlorobenzyl ester, p-bromobenzyl ester, p-methoxybenzyl ester or the like; lower aliphatic acyloxyalkyl ester such as acetoxymethyl ester, acetoxyethyl ester, propionyloxymethyl ester, n- or iso-butyryloxymethyl ester or the like.

According to Process (a) of the reaction scheme (A), the compound of formula (IV) is obtained by reacting the compound (II) with the compound (III).

The reaction of the compound (II) with the compound (III) may be carried out, for instance, by reacting the compound (II) with approximately 0.5 molar to approximately 5 molar, preferably from approximately 0.8 molar to approximately 3 molar in amount of the compound (III) in an appropriate solvent such as tetrahydrofuran, dichloromethane, dioxane, dimethylformamide, dimethylsulfoxide, acetonitrile, hexamethylphosphoramide or the like, preferable in the presence of a base such as sodium hydrogen carbonate, potassium carbonate, triethylamine, diisopropylethylamine, especially diisopropylethylamine, at a temperature ranging from approximately −40° C. to 25° C., preferably under ice-cooling for approximately 30 minutes to 24 hours.

Although it is not required, this reaction is preferred to be carried out in an inert atmosphere, for example in an atmosphere of nitrogen gas or argon gas.

The reaction described above provides the resulting compound of formula (IV), and the resultant may be used for the next reaction without further purification; or the compound (IV) may be isolated and purified in conventional manner such as by means of filtration, extraction, washing, removal of the solvent, drying, column chromatography and so on.

Next, according to Process (b), the compound of the formula (IV) obtained by Process (a) described above is converted to the carbapenem compound of the present invention of the formula (I) by the removal reaction of the carboxyl protecting group known per se, such as solvolysis or hydrogenolysis.

In a typical reaction, the compound of the formula (IV) may be treated in a mixture solvent having pH ranging from 5 to 7, using hydrogen under approximately 1 to 5 atmospheric pressures, in the presence of a catalyst for hydrogenation such as platinum oxide, palladium-activated carbon or palladium hydroxide-activated carbon at temperature ranging from approximately 0° C. to 50° C. for approximately 0.25 to 5 hours. Examples of the mixture solvent used in the reaction may be an acetate buffer solution having pH ranging 5 to 7, a morpholinepropanesulfonic acid-sodium hydroxide buffer solution having pH ranging 5 to 7, or phosphoric acid buffer solution having pH ranging 5 to 7, or further containing alcoholic solvent and/or tetrahydrofuran. Furthermore, tetrahydrofuran-water, tertahydrofuran-ethanol-water, dioxane-water, dioxane-ethanol-water, n-butanol-water containing potassium phosphate dibasic, sodium phosphate dibasic or sodium bicarbonate or the like may be used for the reaction mixture solvent.

Furthermore, the removal of the protecting group $R^1$ may also be carried out by reacting the compound of formula (IV) with zinc in a buffer solution. In typical reaction, the compound of formula (IV) may be treated with zinc in the buffer solution of pH 5 to 7 such as a phosphate buffer solution, an acetate buffer solution, morpholinepropanesulfonate buffer solution, and N-methylmorpholine buffer solution.

Zinc used in the reaction may include, for example, elemental zinc in the form of powder, flower or granule or the like. The amount of zinc used in this reaction is not strictly limited; however, it is conveniently about 1 to 10 parts by weight, preferably 1 to 5 parts by weight per part by weight of the compound of formula (IV) to be treated.

In this reaction, an organic solvent may be used in combination. Examples of the solvent are alcohols such as ethanol, propanol, n-butanol and the like; ethers such as diethylether, tetrahydrofuran, dioxane and the like; acetonitrile, dimethylformamide, dimethylacetamide and the like. Usually, the reaction may be finished in approximately 0.1 to 5 hours in a reaction temperature from about −20° C. to about 50° C., preferably from the room temperature to about 30° C.

Furthermore, the compound of the present invention in which the group "R" is hydrogen atom may be prepared from the compound of formula (III) in which the group "R" is amino protective group, such as p-nitrobenzyloxycarbonyl group (PNZ) or tert-butoxycarbonyl group (Boc), in accordance with the condensation reaction of step (a) in Reaction Scheme A above and then, the removal reaction of the amino and carbonyl protecting groups of the resulting compounds in step (b).

The removal of both amino and carbonyl protecting groups may be preferably conducted by hydrogenolysis as already described in step (b) as mentioned above.

The carbapenem compounds of the formula (I) according to the present invention thus obtained may be isolated and purified by the conventional manner, or by using ion-exchange chromatography or synthetic absorbent polymer resin chromatography method, if necessary.

The compounds of the formula (III) used in the above procedure as the starting compounds, may be prepared in accordance with the processes as illustrated by the reaction scheme B shown below.

Reaction Scheme B

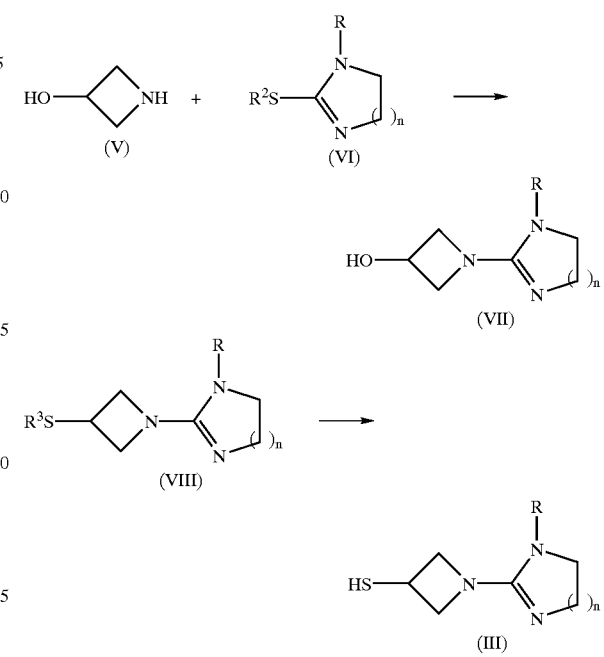

wherein $R^2$ and $R^3$ are thiol protecting groups.

For example, the compound (VII), which may be obtained by the condensation reaction of 3-hydroxyazetidine (V) with compound (VI) having methylthio group in the molecule, is converted to the compound (VIII) under Mitsunobu's reaction condition such as by treating with thioacetic acid. Thus, hydroxy group of the compound (VII) is converted to protected mercapto group, which is protected by thiol protecting group (acetyl group).

Then, the obtained compound (VIII) is converted to the objective compound (III) by removal of the thiol protecting group of the compound (VIII). In the process of the synthesis of the carbapehem compound of formula (I) as shown in the Reaction Scheme A, the crude compound (III) which is obtained by removal of the thiol protecting group of the compound (VIII) can be used for the reaction with compound (II) without purification.

Each process of the Reaction Scheme B may be carried out in the presence of an appropriate inert solvent or catalyst. Examples of the solvent are alcohols such as methanol, ethanol, isopropanol and the like; ethers such as diethylether, tetrahydrofuran, dioxane and the like; benzenes such as benzene, toluene, xylen and the like; acetonitrile, dimethylformamide and the like.

The detailed reaction conditions of the processes of the Reaction Scheme B are described by the Preparation Examples mentioned later, and various kinds of compounds of formula (III) may be obtained by the same manner as described in the Preparation Examples.

The carbapenem compounds of the present invention are novel compounds that are not disclosed specifically in the prior publication, and have superior antibacterial activities. The remarkably high antibacterial activities of the compounds according to the present invention have been proved by antibacterial tests described below.

[Antibacterial Tests]
1. Test Procedures

The antibacterial activities were tested by an agar plate dilution method in accordance with the standard method of The Japanese Chemotherapy Society [Chemotherapy, Vol.29, 76–79(1981)]. A Mulluer-Hinton (MH) agar liquid medium of a test microorganism was cultured overnight at 37° C. and the resultant culture medium was diluted with a buffered saline gelatin (BSG) solution to contain approximately $10^6$ cells of the test microorganisms per milliliter, and then the diluted solution was inoculated with a microplanter at the rate of approximately 5 μl on a MH agar medium containing a test compound. This medium was then incubated at 37° C. for 18 hours. The minimum inhibitory concentration (MIC) is determined as a minimum concentration in which no test microorganism could grow.

It is noted here that the test organisms used were all standard strains, and test compounds were Compound (8) and (15) obtained in Examples mentioned later.

2. Results

Table 1 shows the test results.

TABLE 1

| | MIC (μg/ml) | |
|---|---|---|
| | Test Compounds | |
| Test Organisms | Compound (8) | Compound (15) |
| S. aureus FDA 209 JC-1 | 0.025 | 0.025 |
| S. aureus Terajima | 0.013 | ≦0.006 |
| S. aureus MS 353 | 0.013 | 0.013 |
| S. pyogenes Cook | ≦0.006 | ≦0.006 |
| B. subtilis ATCC 6633 | 0.025 | 0.025 |
| M. luteus ATCC 9341 | 0.025 | 0.05 |
| E. coli NIHJ JC-2 | 0.025 | 0.025 |
| E. coli K-12 C600 | 0.1 | 0.2 |
| E. cloacae 963 | 0.1 | 0.05 |
| E. aerogenes ATCC 13048 | 0.1 | 0.1 |
| K. pneumoniae PCI-602 | 0.1 | 0.05 |
| S. typhimurium 11D971 | 0.05 | 0.05 |
| S. typhi 901 | 0.025 | 0.025 |
| S. paratyphi 1015 | 0.1 | 0.1 |
| S. schottmuelleri 8006 | 0.1 | 0.1 |
| S. enteritridis G14 | 0.2 | 1.56 |
| M. morganii IFO 3848 | 0.2 | 1.56 |
| P. mirabilis IFO 3849 | 0.78 | 0.78 |
| P. vulgaris OX-19 | 0.2 | 0.78 |
| P. vulgalis HX-19 | 0.39 | 0.78 |
| P. rettgeri IFO 3850 | 0.05 | 0.025 |
| P. aeruginosa IFO 3445 | 3.13 | 1.56 |
| P. aeruginosa NCTC 10490 | 12.5 | 1.56 |
| P. aeruginosa PAO 1 | 12.5 | 3.13 |

The foregoing results clearly demonstrate that the carbapenem compounds according to the present invention have superior antibacterial activities.

Furthermore, the compounds of the present invention are characterized by having a methyl group introduced at 1 β-position and specific 1-aza-3-thiabicyclo ring group at the 2-position of carbapenem skeleton, and therefore are stable against renal dehydropeptidase (DHP) and are also stable chemically and physically.

[Toxicity Tests]

Toxicological studies were carried out using a group of 10 male mice of ddY strain weighing from 20 to 23 grams. Solutions containing each of the carbapenem compounds of the present invention obtained by Examples mentioned later were administered subcutaneously to the mice and subjected to observations for one week. The results have revealed that the groups of mice to which the carbapenem compounds of the present invention had been administered in the amount of 500 mg/kg were alive without any abnormal findings.

As described above, the carbapenem compounds according to the present invention permit a single administration without combining with any other DHP inhibitor, and are extremely useful as antibacterial agents for therapy and prevention of infectious diseases from various pathogenic organisms.

The carbapenem compounds or pharmaceutically acceptable salt thereof according to the present invention may be administered as an antibacterial agent to the human being and other mammalian animals in the form of a pharmaceutically acceptable composition containing an antibacterial effective amount thereof. The administration dose may vary in a wide range with age, weight, conditions of patients, forms or route of administration, physician's diagnoses or the like and may be orally, parenterally or topically administered. To adult patients, a standard daily dose range from approximately 200 to approximately 3,000 mg once or in several installments per day.

The pharmaceutically acceptable composition of the carbapenem compounds according to the present invention may contain an inorganic or organic, solid or liquid carrier or diluent, which is conventionally used for preparation of medicines, particularly antibiotic preparations, such as an excipient, e.g., starch, lactose, white sugar, crystalline cellulose, calcium phosphate or the like; a binder, e.g., acacia, hydroxypropyl cellulose, alginic acid, gelatin, polyvinyl pyrrolidone or the like; a lubricant, e.g., stearic acid, magnesium stearate, talc, hydrogenated plant oil or the like; a disintegrator, e.g., modified starch, calcium carboxymethyl cellulose, low substituted hydroxypropyl cellulose or the like; or a dissolution aid, e.g., a non-ionic surfactant, an anionic surfactant or the like, and may be prepared into forms suitable for oral, parenteral or topical administration.

The formulation suitable for oral administration may include solid preparations such as tablets, coatings, capsules, troches, powders, fine powders, granules, dry syrups or the like, and liquid preparations such as syrups and the like; the formulations suitable for parenteral administration may include, for example, injectable solutions, drip-feed solutions, depositories or the like; and the formulations suitable for topical administration may include, for example, ointments, tinctures, creams, gels or the like. These formulations may be formed by procedures known per se to those skilled in the art in the field of pharmaceutical formulations.

The carbapenem compounds according to the present invention are suitable for administeration in the form of parenteral formulations, particularly in the form of injectable solutions.

EXAMPLES

The carbapenem compounds according to the present invention will be described more in detail by way of preparation examples, working examples and formulation examples; however, the present invention is not limited to these examples.

In the following description, the following symbols are used to represent the particular meanings respectively.

Me: methyl group

Ac: acetyl group

Ms: methanesulfonyl group

Tri: trityl group

PNB: p-nitrobenzyl group

PNZ: p-nitrobenzyloxycarbonyl group

Preparation 1

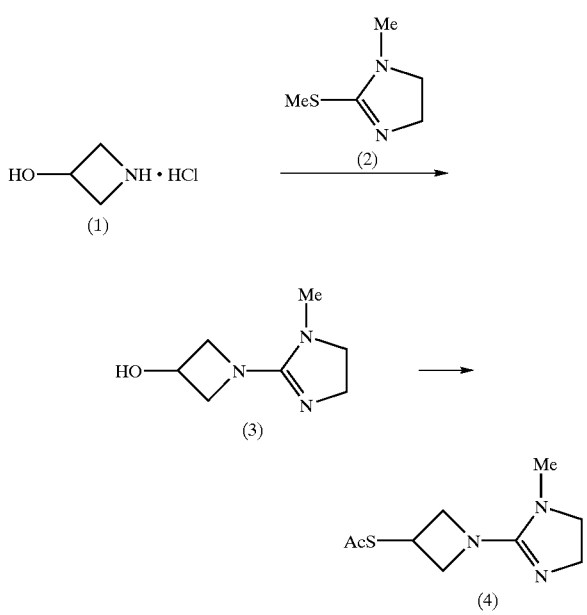

(a) A mixture of 654 mg of 3-hydroxyazetidine hydrochloride [Compound (1)] and 1.56 g of 2-methylthio-1-methylimidazoline [Compound (2)] was heated at 80° C. under stirring for 30 minutes. After the reaction, the reaction mixture was washed with ether, dissolved in the small amount of methanol, and further dissolved in dichloromethane, and then washed with 50% aqueous potassium carbonate solution. The resulting organic layer was dried over anhydrous sodium sulfate and the solvent was removed under reduced pressure to give 841 mg (yield: 90%) of Compound (3) as oily substance.

$^1$H-NMR (270 MHz; CDCl$_3$) δ: 2.67(s, 3H), 3.32(t, 2H, J=8.25 Hz), 3.56(t, 2H, J=8.25 Hz), 3.84(dd, 2H, J=4.95 & 8.91 Hz), 3.90(br, 1H), 4.18(dd, 2H, J=6.60 & 8.91 Hz), 4.58–4.62(m, 1H).

(b) To a solution of 717 mg of triphenylphosphine in 4 ml of anhydrous tetrahydrofuran was added 0.41 ml of diethyl azodicarboxylate under ice-cooling, and the reaction mixture was stirred for 30 minutes. Then, to this reaction mixture was added dropwise a mixture solution of 134 mg of Compound (3) obtained above and 0.185 ml of thioacetic acid in 20 ml of anhydrous tetrahydrofuran under ice-cooling, and the reaction mixture was stirred for 1 hour under the same conditions, then for 1 hour at room temperature. After the reaction solvent was removed under reduced pressure, the resulting residue was purified by silica gel column chromatography (eluted solvent; methanol/chloroform) to give 150 mg (yield: 82%) of Compound (4).

$^1$H-NMR (270 MHz; CDCl$_3$) δ: 2.36(s, 3H), 2.95(s, 3H), 3.70–3.80(m, 4H), 4.30–4.40(m, 1H), 4.44(dd, 2H, J=5.61 & 8.91 Hz), 5.05(dd, 2H, J=8.58 & 8.91 Hz).

Example 1

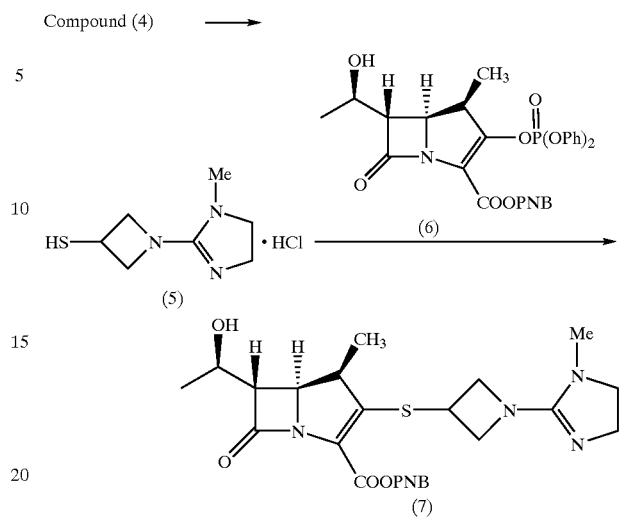

To a solution of 740 mg of Compound (4) obtained in the step (b) of Preparation 1 in 12 ml of anhydrous methanol was added 670 mg of 28% sodium methoxide-methanol solution under ice-cooling and nitrogen gas stream. Then the reaction mixture was stirred for 5 minutes under the same conditions. After the reaction, 3.5 ml of 2N-HCl-methanol was added to the reaction mixture and the solvent was removed under reduced pressure to give the crude Compound (5), and this crude Compound (5) was used for the next reaction without further purification. The crude Compound (5) was dissolved in 5 ml of acetonitrile and the unsolved substance was removed by filtration. Then, this filtrate was added to a mixture solution of 2.063 g of Compound (6) in 35 ml of anhydrous acetonitrile, and 1.2 ml of diisopropylethylamine was further added dropwise to the reaction mixture under ice-cooling, then the mixture was stirred for 2 hours under the same conditions. The separated solids were collected by filtration and washed with dichloromethane and dried in vacuum to give 1.05 g (67% total yield) of hydrochloride salt of Compound (7) as crystalline.

$^1$H-NMR(270 MHz; CD$_3$OD) δ:1.23(d, 3H, J=7.25 Hz), 1.29(d, 3H, J=6.27 Hz), 2.97(s,3H),3.20–3.40(m, 2H), 3.50–3.80(m,4H), 4.12(q,1H, J=6.27 Hz), 4.20–4.30(m, 3H), 4.30–4.50(m, 1H), 4.80–4.90(m, 2H), 5.30 & 5.47(AB, 2H, J=13.86 Hz), 7.72(d, 2H, J=8.91 Hz), 8.23(d, 2H, J=8.91 Hz).

Example 2

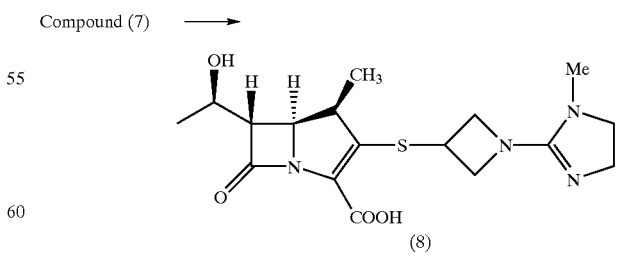

To a mixture solution of 200 mg of Compound (7) obtained in Example 1 in 7 ml of n-butanol were added 10% of palladium-carbon (50% hydrated) and 7 ml of 0.1 M phosphate buffer solution (pH 6.4). Then, the mixture was vigorously stirred under hydrogen gas atmosphere (4 kg/cm²) for 1.5 hours. After the reaction, unsolved substance was removed by using Celite and the obtained filtrate was concentrated under reduced pressure. The resulting residue was purified by using Diaion HP-40 column (eluted solvent; 6% isopropylalcohol-water) to give 116 mg (yield: 87%) of Compound (8).

¹H-NMR (270 MHz; D₂O) δ: 1.20(d, 3H, J=7.26 Hz), 1.32(d, 3H, J=6.3 Hz), 2.97(s, 3H), 3.22(dq, 1H, J=7.26 & 8.91 Hz), 3.46(dd, 1H, J=2.64 & 6.27 Hz), 3.60–3.78(m, 4H), 4.20–4.37(m, 5H), 4.73–4.83(m, 2H).

Preparation 2

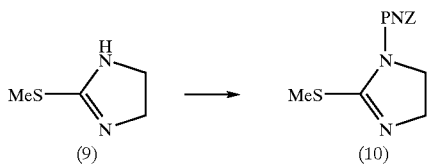

To a mixture solution of 1.16 g of 2-methylthio-1,3-imidazoline [Compound (9)] and 1.42 g of diisopropylamine in 30 ml of anhydrous dichloromethane was added dropwise 4.17 g of dioxane solution containing 51.7% p-nitrobenzyl chloroformate at −15° C. Then, the reaction mixture was stirred for 1 hour under the same conditions and for 1 hour at 0° C. After the reaction, the reaction mixture was washed with saturated sodium hydrogen carbonate aqueous solution and saturated saline solution, and dried. The solvent was removed under reduced pressure and the resulting residue was washed with ether to give 2.52 g (yield: 86%) of Compound (10).

¹H-NMR (270 MHz; CDCl₃) δ: 2.43(s, 3H), 3.94(s, 4H), 5.31(s, 2H), 7.56(d, 2H, J=8.6 Hz), 8.25(d, 2H J=8.6 Hz).

Preparation 3

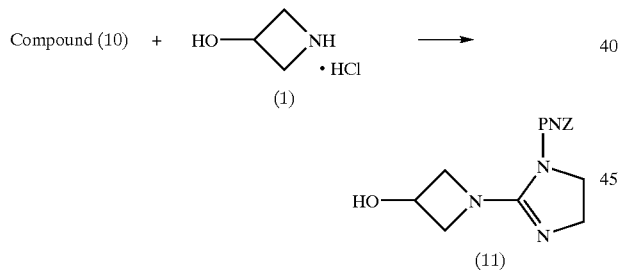

A mixture solution of 1.54 g of Compound (10) obtained in Preparation 2 above and 0.68 g of 3-hydroxyazetidine hydrochloride [Compound (1)] in 30 ml of ethanol was refluxed for 3 hours. After removal of the solvent under reduced pressure, the resulting residue was treated with a mixture solution of 50% aqueous potassium carbonate solution and dichloromethane. The organic layer was separated and after drying the solvent was removed under reduced pressure. The resulting residue was purified by silica gel column chromatography (eluted solvent; ethanol/chloroform=1/4) to give 1.31 g (yield: 79%) of Compound (11).

¹H-NMR (270 MHz; CDCl₃) δ: 3.64(d, 1H, J=8.3 Hz), 3.67(d, 1H, J=8.6 Hz), 3.87(dd, 2H, J=5.0 & 9.8 Hz), 3.92(d, 1H, J=8.6 Hz), 3.95(d, 1H, J=8.3 Hz), 4.27(dd, 2H, J=6.6 & 9.8 Hz), 4.56–4.65(m, 1H), 5.27(s, 2H), 7.54(d, 2H, J=8.9 Hz), 8.24(d, 2H, J=8.9 Hz).

Preparation 4

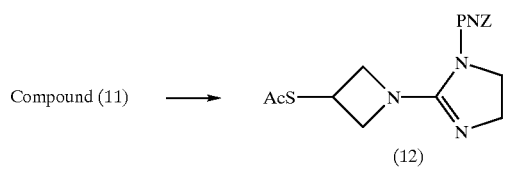

To a mixture solution of 1.69 g of Compound (11) obtained in the Preparation 3 above and 3.83 g of triphenylphosphine in 35 ml of anhydrous tetrahydrofuran was added dropwise 2.48 g of diethyl-azodicarboxylate at 0° C., and the reaction mixture was stirred for 30 minutes under the same conditions. Then, 1.09 g of thioacetic acid was added to the reaction mixture and the reaction mixture was stirred for 1 hour at 0° C. After removal of the solvent under reduced pressure, the resulting residue was purified by silica gel column chromatography (eluted solvent; chloroform/acetone=3/1; then, chloroform/methanol=9/1) to give 1.27 g (yield: 64%) of Compound (12).

¹H-NMR (270 MHz; CDCl₃) δ: 2.32(s, 3H), 3.70(t, 2H, J=8.6 Hz), 3.91–3.97(m, 4H), 4.17–4.36(m, 1H), 4.49(t, 2H, J=8.6 Hz), 5.26(s, 2H), 7.54(d, 2H, J=8.9 Hz), 8.25(d, 2H, J=8.9 Hz).

Example 3

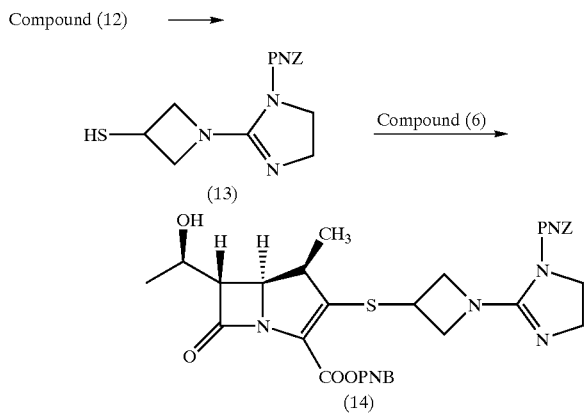

0.65 g of 28% sodium methoxide-methanol solution was added to a mixture solution of 1.27 g of Compound (12) obtained in Preparation 4 above in 20 ml of anhydrous methanol under −15° C., and the reaction mixture was stirred for 5 minutes under the same conditions. After the reaction, 3.4 ml of 2N-HCl-methanol solution was added to the reaction mixture and the solvent was removed under reduced pressure to give the crude Compound (13). This crude Compound (13) was used for the next step without further purification. The crude Compound (13) was suspended in 10 ml of acetonitrile, and to this suspension was added a mixture solution of 1.89 g of Compound (6) in 40 ml of anhydrous acetonitrile, and further added 620 mg of diisopropylethylamine at −15° C., respectively, and the reaction was stirred for 2 hours. After removal of the solvent, the resulting residue was dissolved in ethyl acetate and the organic layer was washed with saturated sodium hydrogen carbonate aqueous solution and saturated saline solution. The solvent was removed under reduced pressure and the resulting residue was purified by silica gel column chromatography (eluted solvent; chloroform/ethanol=10/1) to give 423 mg (yield: 20%) of Compound (14).

¹H-NMR (270MHz; CDCl₃) δ: 1.22(d, 3H, J=7.3 Hz), 1.35(d, 3H, J=6.3 Hz), 3.16(dq, 1H, J=7.3 & 8.9 Hz), 3.26(dd, 1H, J=2.6 & 6.6 Hz), 3.69(d, 1H, J=7.6 Hz), 3.72(d, 1H, J=7.3 Hz), 3.91–4.12(m, 3H), 4.18–4.28(m, 2H), 4.43(d, 1H, J=7.6 Hz), 4.46(d, 1H, J=7.3 Hz), 5.24(s, 2H), 5.26(d, 1H, J=13.9 Hz), 5.52(d, 1H, J=13.9 Hz), 7.53(d, 2H, J=8.6 Hz), 7.67(d, 2H, J=8.9 Hz), 8.22(d, 2H, J=8.9 Hz), 8.25(d, 2H, J=8.6 Hz).

Example 4

Compound (14) →

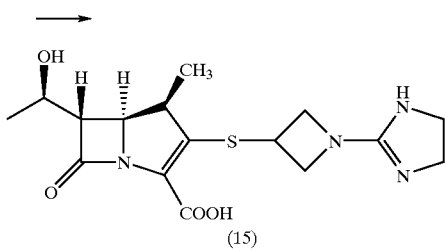

(15)

423 mg of Compound (14) obtained in Example 3 above was dissolved in 15 ml of butanol and 15 ml of 0.1M acetate buffer solution (pH 6.6), and to this mixture was added 100 mg of 10% palladium-carbon. Then, the reaction mixture was vigorously stirred for 1.5 hours under hydrogen gas atmosphere (4 kg/cm²). Then the catalyst was removed off by filtration and the filtrate was concentrated under reduced pressure. The resulting residue was purified by using Diaion HP-40 column (eluted solvent; 5%-isopropylalcohol/water) to give 133 mg (yield: 59%) of Compound (15).

¹H-NMR (270 MHz; D₂O) δ: 1.18(d, 3H, J=7.3 Hz), 1.30(d, 3H, J=6.3 Hz), 3.18(dq, 1H, J=7.3 & 8.9 Hz), 3.44(dd, 1H, J=2.3 & 5.9 Hz), 3.72(s, 4H), 4.06(dd, 2H, J=4.3 & 8.6 Hz), 4.10(dd, 1H, J=2.3 & 8.9 Hz), 4.19–4.37(m, 3H), 4.61(t, 2H, J=8.6 Hz).

Preparation 5

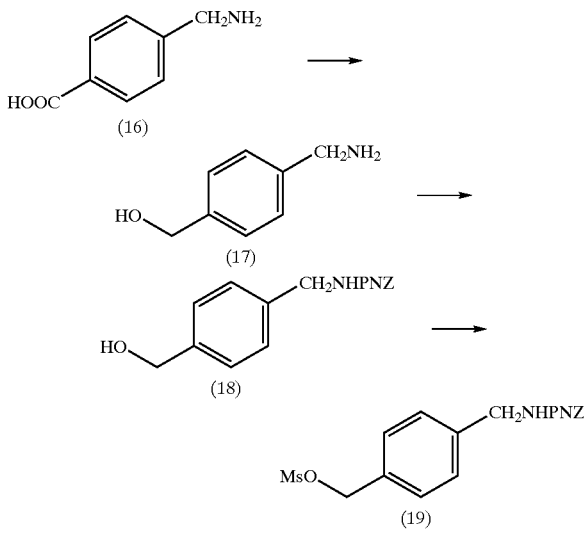

(a) To a mixture solution of 9.238 g (61.1 mmol) of 4-aminobenzylamine [Compound (16)] in 108 ml of tetrahydrofuran was added 4.618 g (122.1 mmol) of lithium aluminum hydride and the reaction mixture was stirred for 24 hours at the room temperature. After the reaction, 50% potassium carbonate aqueous solution was added to the reaction mixture at 0° C. and filtrated by using Celite. The filtrate was extracted with dichloromethane and the organic layer was washed with saturated saline solution and dried over potassium carbonate. The solvent was removed under reduced pressure to give 6.184 g (yield: 73.8%) of 4-aminomethylbenzyl alcohol [Compound (17)].

¹H-NMR (CDCl₃) δ: 1.73(bs, 3H), 3.84(s 2H), 4.67(s, 2H), 7.29(d, 2H, J=8.1 Hz), 7.33(d, 2H J=8.1 Hz).

(b) To a mixture of 6.123 g (44.6 mmol) of 4-aminomethylbenzyl alcohol [Compound (17)] obtained in the step (a) above and 9.75 g (116 mmol) of sodium hydrogen carbonate in 20 ml of water and 80 ml of dioxane was added 25.7 ml (58.0 mmol) of dioxane solution containing 48.7% p-nitrobenzyl chloroformate and the reaction mixture was stirred for 2 hours under nitrogen gas stream. After the reaction, water was added to the reaction mixture and the mixture was extracted with chloroform. The organic layer was washed with saturated saline solution and dried over magnesium sulfate. The solvent was removed under reduced pressure and the resulting crude crystalline was washed with ethyl acetate to give 14.1 g (yield: quantitatively) of Compound (18) as pale brownish crystalline.

¹H-NMR (CDCl₃) δ: 1.68(t, 1H, J=5.8 Hz), 4.40(d, 2H, J=6.0 Hz), 4.69(d, 2H, J=5.8Hz), 5.14(s, 1H), 5.23(s, 2H), 7.29(d, 2H, J=8.0 Hz), 7.35(d, 2H, J=8.0 Hz), 7.51(d, 2H, J=8.2 Hz), 8.22(d, 2H, J=8.2 Hz).

(c) To a mixture solution of 12.85 g (40.6 mmol) of Compound (18) obtained in the step (b) above in 200 ml of tetrahydrofuran was added 8.49 ml (60.9 mmol) of triethylamine and 3.77 ml (48.72 mol) of methanesulfonylchloride under 0° C. and the reaction mixture was stirred for 30 minutes under nitrogen gas stream. After the reaction, water was added to the reaction mixture and the mixture was extracted with ethyl acetate. The organic layer was washed with saturated saline solution and dried over magnesium sulfate. The solvent was removed under reduced pressure and the resulting crude crystalline was washed with ethyl acetate to give 13.98 g (yield: 87.3%) of Compound (19) as colorless crystalline.

¹H-NMR (CDCl₃) δ: 2.94(s, 3H), 4.42(d, 2H, J=6.1 Hz), 5.18(s, 1H), 5.23(s, 4H), 7.33(d, 2H, J=8.0 Hz), 7.40(d, 2H, J=8.0 Hz), 7.52(d, 2H, J=8.4 Hz), 8.22(d, 2H, J=8.4 Hz).

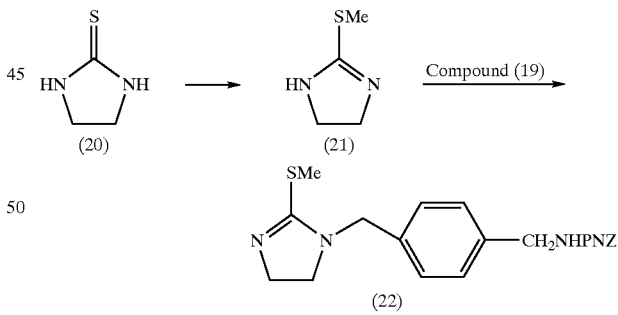

(a) To a mixture solution of 8 g (78.3 mmol) of imidazolidine-2-thione [Compound (20)] in 78 ml of methanol was added 5.85 ml (94.0 mmol) of methyl iodide and the reaction mixture was stirred for 1.5 hours at the room temperature under nitrogen gas stream. After the reaction, the solvent was removed under reduced pressure and the resulting residue was treated with 50 ml of 50% potassium carbonate aqueous solution, then, the mixture was extracted with dichloromethane. The organic layer was dried over potassium carbonate and the solvent was removed under reduced pressure to give 8.86 g (yield: 97.4%) of Compound (21) as colorless crystalline.

$^1$H-NMR (CDCl$_3$) δ: 2.49(s, 3H), 3.67(s, 4H), 4.31(bs, 1H).

(b) A mixture solution of 12 g (30.4 mmol) of Compound (19) obtained in the step (c) of Preparation 5, 4.24 g (36.5 mmol) of Compound (21) obtained above step (a) and 5.09 ml (36.5 mmol) of triethylamine in 61 ml of dichloromethane was stirred for 20 hours at the room temperature under nitrogen gas stream. After the reaction, the solvent was removed under reduced pressure and the resulting residue was treated with ethyl acetate. The organic layer was washed with saturated sodium hydrogen carbonate aqueous solution and saturated saline solution, and dried over magnesium sulfate. The solvent was removed under reduced pressure and the resulting residue was purified by silica gel column chromatography (eluted solvent; chloroform/methanol=from 19/1 to 9/1) to give 6.00 g (yield: 47.5%) of Compound (22) as yellowish oily substance.

$^1$H-NMR (CDCl$_3$) δ: 2.53(s, 3H), 3.27(t, 2H, J=9.3 Hz), 3.76(t, 2H, J=9.3 Hz), 4.28(s, 2H), 4.39(d, 2H, J=6.0 Hz), 5.18(s, 1H), 5.23(s, 2H), 7.27(s, 4H), 7.51(d, 2H, J=8.4 Hz), 8.22(d, 2H, J=8.4 Hz).

Preparation 7

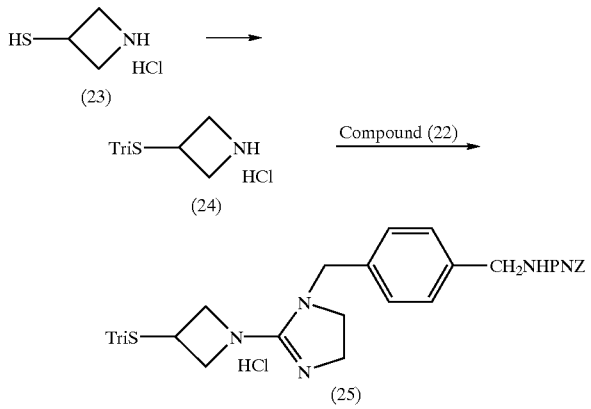

(a) To a mixture solution of 4.05 g (32.2 mmol) of 3-mercaptoazetidine hydrochloride [Compound (23)] in 40 ml of trifluoroacetic acid was added 10.06 g (38.6 mmol) of triphenylmethanol and the mixture was stirred for 1 hour at the room temperature under nitrogen gas stream. After removal of the solvent under reduced pressure, the resulting residue was treated with water and the mixture was extracted with chloroform. The organic layer was washed with saturated saline solution and dried over magnesium sulfate. The solvent was removed under reduced pressure and the resulting residue was purified by silica gel column chromatography (eluted solvent; chloroform/methanol=from 95/5 to 9/1) to give 11.85 g (yield: quantitatively) 3-tritylthioazetidine hydrochloride [Compound (24)] as colorless crystalline.

$^1$H-NMR (CDCl$_3$) δ: 3.50–3.70(m, 5H), 7.20–7.40(m, 15H), 9.39(bs, 1H), 9.70(bs, 1H).

(b) A mixture solution of 5.72 g (13.8 mmol) of Compound (22) obtained in the Preparation 6, 6.09 g (16.56 mmol) of 3-tritylthioazetidine hydrochloride [Compound (24)] obtained above step (a) and 2.49 ml (13.8 mmol) of triethylamine in 138 ml of ethanol was refluxed for 15 hours under nitrogen gas stream. After the reaction, the reaction mixture was concentrated and the resulting residue was purified by silica gel column chromatography (eluted solvent; chloroform/methanol/acetone=8/1/1) to give 7.1 g (yield: 70.1%) of Compound (25) as pale yellowish amorphous.

$^1$H-NMR (CDCl$_3$) δ: 3.49(t, 2H, J=8.9 Hz), 3.55(m, 1H), 3.67(t, 2H, J=8.9Hz), 3.80(dd, 2H, J=6.7 & 8.9 Hz), 4.12(s, 2H), 4.13(m, 2H), 4.42(d, 2H, J=6.2 Hz), 5.23(s, 2H), 5.53(bs, 1H), 7.05(d, 2H, J=7.8 Hz), 7.15–7.29(m, 15H), 7.34(d, 2H, J=7.8 Hz), 7.51(d, 2H, J=8.3 Hz), 7.52(d, 2H, J=8.3 Hz), 10.6(bs, 1H).

Example 5

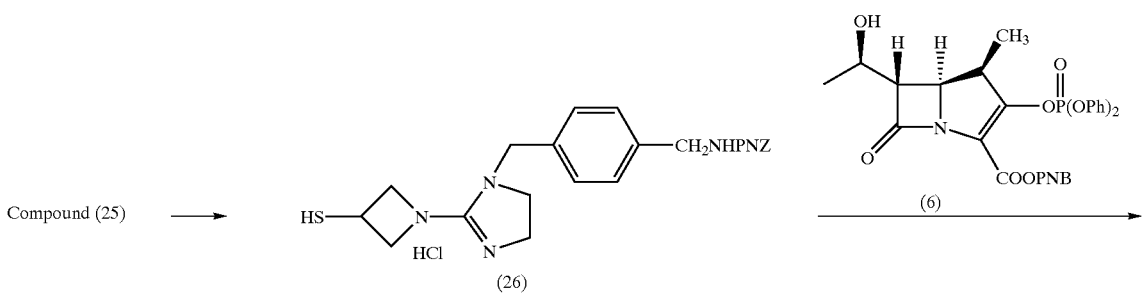

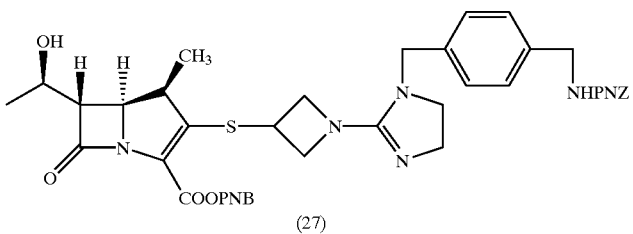

(a) To a mixture solution of 7.07 g (9.62 mmol) of Compound (25) obtained in Preparation 7 in 15 ml of trifluoroacetic acid was added 1.32 g (11.5 mmol) of triethylsilane and the mixture was stirred for 10 minutes at the room temperature under nitrogen gas stream. After the reaction, the reaction mixture was concentrated and the resulting residue was treated with water, and then extracted with chloroform. The organic layer was washed with saturated saline solution and dried over magnesium sulfate. The solvent was removed under reduced pressure and the resulting residue was purified by silica gel column chromatography (eluted solvent; chloroform/methanol=from 9/1 to 2/1) to give 4.32 g (yield: 91.3%) of Compound (26) as brownish oily substance.

$^1$H-NMR (CDCl$_3$) δ: 3.59(t, 2H, J=9.5 Hz), 3.72(t, 2H, J=9.5 Hz), 3.90(m, 1H), 4.27(dd, 2H, J=5.9 & 9.2Hz), 4.38(s, 2H), 4.40(d, 2H, J=6.6 Hz), 4.82(m, 2H), 5.22(s, 2H), 5.81(bs, 1H), 7.18(d, 2H, J=7.3 Hz), 7.35(d, 2H, J=7.3 Hz), 7.52(d, 2H, J=8.5 Hz), 8.18(d, 2H, J=8.5 Hz), 10.24(bs, 1H).

(b) To a mixture solution of 4.32 g (8.78 mmol) of Compound (26) obtained above and 4.32 g (9.66 mmol) of Compound (6) in 88 ml of acetonitrile was added 1.68 ml (9.66 mmol) of diisopropylethylamine at −5° C. and the mixture was stirred for 30 minutes under nitrogen gas stream. After the reaction, the reaction mixture was concentrated under reduced pressure and the resulting residue was purified by silica gel column chromatography (eluted solvent: chloroform/methanol=from 9/1 to 3/1). Then, the obtained compound was dissolved in dichloromethane and the mixture was washed with 10% sodium carbonate aqueous solution and dried. The solvent was removed under reduced pressure to give 4.48 g (yield: 63.8%) of Compound (27) as yellowish amorphous. $^1$H-NMR (acetone-d$_6$) δ: 1.24(d, 3H, J=7.2Hz), 1.26(d, 3H, J=6.3 Hz), 3.22(t, 2H, J=8.9 Hz), 3.32(dd, 1H, J=2.7 & 6.7 Hz), 3.42(m, 1H), 3.52(t, 2H, J=8.9 Hz), 3.91(m, 2H), 4.11(m, 1H), 4.12(s, 2H), 4.25–4.29(m, 4H), 4.44(dd, 2H, J=8.0 & 16.2Hz), 5.26(s, 2H), 5.43(dd, 2H, J=14.1 & 95.5 Hz), 7.07(s, 1H), 7.28(d, 2H, J=8.4 Hz), 7.31(d, 2H, J=8.4 Hz), 7.66(d, 2H, J=8.5 Hz), 7.81(d, 2H, J=8.8 Hz), 8.23(d, 2H, J=8.5 Hz), 8.24(d, 2H, J=8.8 Hz).

Example 6

Compound (27) ⟶

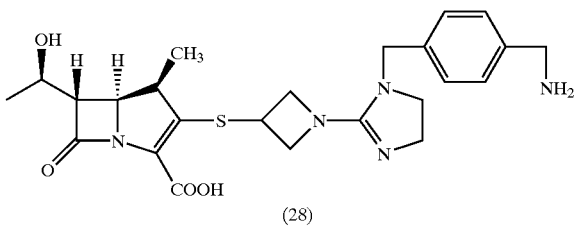

(28)

A mixture of 2 g (2.50 mmol) of Compound (27) obtained above and 1 g of 10% palladium-carbon (50% hydrated) in 100 ml of 0.5M-phosphate buffer solution and 100 ml of tetrahydrofuran was stirred for 2. hours under hydrogen gas atmosphere (400 kPa). After the reaction, the reaction mixture was filtrated and pH of the resulting filtrate was adjusted to 6.0 and then washed with water-butanol. The water layer was separated and pH of this water layer was adjusted to 6.0 again and concentrated under reduced pressure. The resulting residue was purified using HP-21 resin column chromatography (eluted solvent; water/acetonitrile=from 1/0 to 85/15) and obtained eluted parts were concentrated under reduced pressure and then lyophilized to give 237 mg (yield: 19.6%) of Compound (28) as yellowish amorphous.

$^1$H-NMR (D$_2$O) δ: 1.11(d, 3H, J=6.8 Hz), 1.18(d, 3H, J=6.4 Hz), 2.87(m, 1H), 3.32(dd, 1H, J=2.5 & 5.8 Hz), 3.60–4.20(m, 12H), 4.50–4.80(m, 3H), 7.31(d, 2H, J=8.1 Hz), 7.41(d, 2H, J=8.1 Hz).

IR (KBr): 1755, 1645 cm$^{-1}$.

$\lambda^{max}$ (MeOH): 203, 209 nm.

The following are formulation of the carbapenem compounds according to the present invention.

Formulation Example 1 (Injection)

(1) Injectable suspension

| | |
|---|---|
| Compound (8) | 250 mg |
| Methyl cellulose | 500 mg |
| Polyvinyl pyrrolidone | 50 mg |
| Methyl p-oxybenzoate | 100 mg |
| Polysorvate 80 | 100 mg |
| Lidocain hydrochloride | 500 mg |
| Distilled water | optimum |
| Total volume | 100 ml |

The above components were formulated into 100 ml of an injectable suspension.

(2) Lyophilization

An appropriate amount of distilled water was added to 20 g of Compound (8) to make a total volume of 1000 ml. 2.5 ml or 5 ml of above solution [each solution contain 500 mg or 1000 mg of the Compound (8), respectively] was filled in vials and lyophilized. The lyophilized vial was mixed in situ with approximately 3–4 ml of distilled water to make an injectable solution.

(3) Powder

Compound (15) was filled in an amount of 250 mg in a vial and mixed in situ with approximately 3–4 ml of distilled water to make an injectable solution.

Formulation Example 2 (Tablets)

| | |
|---|---|
| Compound (8) | 250 mg |
| Lactose | 250 mg |
| Hydroxypropyl cellulose | 1 mg |
| Magnesium stearate | 10 mg |
| | 511 mg/tablet |

The above components were kneaded and granulated in conventional manner, then tabletted to produce tablets. Resulting tablets may be converted to sugar or film coated tablets in conventional manner.

Formulation Example 3 (Capsules)

| | |
|---|---|
| Compound (15) | 500 mg |
| Magnesium stearate | 10 mg |
| | 510 mg/capsule |

The components were mixed with each other and filled in conventional hard gelatin capsules.

INDUSTRIAL APPLICABILITY

As described above, according to the present invention, it is provided newly carbapenem compounds having high antibacterial activities and are excellent in resisting renal dehydropeptidase.

What is claimed is:

1. Carbapenem compounds represented by the following formula (I):

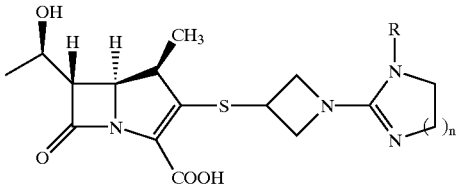

wherein
R is hydrogen atom, or substituted or unsubstituted lower alkyl group; and,
n is an integer of 1 or 2,
and ester thereof or a pharmaceutically acceptable salt thereof.

2. An antibacterial agent containing the carbapenem compounds, ester thereof or pharmaceutically acceptable salt thereof claimed in claim 1 as an active ingredient.

3. Carbapenem compounds represented by the following formula (I):

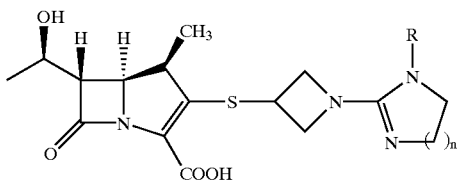

wherein R is hydrogen atom, or a lower alkyl group; and n is an integer of 1 or 2, and
an ester thereof or a pharmaceutically acceptable salt thereof.

4. Carbapenem compounds according to claim 1, wherein the lower alkyl is substituted by a hydroxy group; a lower alkoxy group; a halogen atom; an amino group; a phenyl; a nitro group; or an acetyl group.

5. Carbapenem compounds according to claim 4, wherein the amino group is selected from the group consisting of dimethylamino, diethylamino, and methylethylamino.

6. Carbapenem compounds according to claim 4, wherein the phenyl is selected from the group consisting of hydroxyphenyl, methylphenyl, dimethylphenyl, aminophenyl, aminomethylphenyl, and nitrophenyl.

* * * * *